United States Patent [19]
Berkoff et al.

[11] 4,092,352
[45] May 30, 1978

[54] 2,3-DICHLORO-4-HYDROXY-BENZOIC ACID AND PROCESS FOR PREPARATION THEREOF

[75] Inventors: Charles E. Berkoff, Huntingdon Valley; Robert Lee Webb, West Chester, both of Pa.

[73] Assignee: SmithKline Corporation, Philadelphia, Pa.

[21] Appl. No.: 729,329

[22] Filed: Oct. 4, 1976

[51] Int. Cl.$^2$ .............................................. C07C 65/04
[52] U.S. Cl. .......................... 260/521 H; 260/332.2 R
[58] Field of Search ..................................... 260/521 H

[56] References Cited

U.S. PATENT DOCUMENTS 2,811,547  10/1957  Brown ............................ 260/521 H

OTHER PUBLICATIONS

Chem. Abstr., 77100u, vol. 68, 1968.
Chem. Abstr., 53271y, vol. 74, 1971.

*Primary Examiner*—Paul J. Killos
*Attorney, Agent, or Firm*—William H. Edgerton

[57] ABSTRACT

A Reimer-Tiemann reaction of 2,3-dichlorophenol with carbon tetrachloride gives 2,3-dichloro-4-hydroxy-benzoic acid, a novel intermediate, which is then reacted with thiophene in the presence of phosphorus pentoxide or polyphosphoric acid to give 2,3-dichloro-4-(2-thienoyl)-phenol. This compound is then converted to the diuretic, ticrynafen, by known prior art reactions.

2 Claims, No Drawings

2,3-DICHLORO-4-HYDROXY-BENZOIC ACID AND PROCESS FOR PREPARATION THEREOF

This invention comprises a novel synthetic route and a novel intermediate for preparing the diuretic, ticrynafen (tienilic acid). The reported methods for preparing ticrynafen contain as one step in the reaction sequence, a Friedel-Crafts acylation of 2,3-dichloroanisole with thienoyl chloride or of thiophene with 4-methoxy-2,3-dichlorobenzoyl chloride [see Eur. J. Med. Chem. — Chimica Therapeutica, 9 (6), 625-633 (1974) or, in part, U.S. Pat. No. 3,758,506].

The present invention employs relatively inexpensive starting materials involving new chemical reactions and a new versatile intermediate.

The first step of this invention comprises the reaction of 2,3-dichlorophenol with carbon tetrachloride under Reimer-Tiemann conditions. To our knowneldge this reaction is unreported in the prior art. The art teaches that isomeric dichlorophenols react with carbon tetrachloride in the Reimer-Tiemann reaction very poorly if at all. For example 2,6or 2,4-dichlorophenols give less than 5% yield of the carboxylic acids. See Suzuki, H. et al., Chem. Abst. 76, 126-537t. The reason given by Suzuki for such low yields was that "Polychloro compounds" had "low reactivity" in the reaction.

We have now found that 2,3-dichlorophenol gives yields of about 70% of the desired carboxylated product when reacted with carbon tetrachloride under Reimer-Tiemann conditions. This unexpected yield of 2,3-dichloro-4-hydroxybenzoic acid is obtained by reacting 2,3-dichlorophenol with carbon tetrachloride in the presence of a copper source such as copper powder, copper bronze, etc. and aqueous alkali hydroxide such as sodium or potassium hydroxide most conveniently at reflux temperature until reaction is complete. The time of the reaction varies but a reflux period of from 6-48 hours is most often used. The product is isolated by standard chemical methods.

The resulting product is the new intermediate, 2,3-dichloro-4-hydroxybenzoic acid. This intermediate is converted to its methyl ether which can, in turn, be converted to ticrynafen by chemical methods of the art referred to above.

In another aspect of this invention we have now found that 2,3-dichloro-4-hydroxybenzoic acid can be condensed under Friedel-Crafts conditions with thiophene to give 2,3-dichloro4-(2-thienoyl)-phenol. The reaction is run by reacting an excess of thiophene with the hydroxybenzoic acid intermediate in the presence of phosphorus pentoxide or polyphosphoric acid (phosphorus pentoxide in phosphoric acid) most conveniently at the reflux temperature for from about 1-8 hours. The solvent may be any inert solvent in which the reactants are soluble for example the common benzenoid, ether or halogenated hydrocarbon solvents such as benzene, toluene, chlorobenzene, xylene, methylene chloride, dichloroethane, chloroform, carbon tetrachloride and other common Friedel-Crafts solvents. The yields are from about 30% to 60%.

The advantage of this aspect of the claimed invention is that inexpensive thiophene rather than thiophene-2-carboxylic acid chloride is used as starting material. Also the demethylation step after condensation is avoided. This is necessary when the condensation was run on 4-methoxy-2,3-dichlorobenzoic acid as reported in the prior art.

The 2,3-dichloro-4-(2-thienoyl)-phenol thusly produced is then used as an intermediate to produce ticrynafen as described in U.S. Pat. No. 3,758,506.

The following examples are designed to illustrate the practice of this invention but not to limit the scope of the invention. All temperatures are on the Centigrade scale.

EXAMPLE 1

2,3-Dichloro-4-hydroxybenzoic Acid

A 250 ml flask was charged with 33 g (0.2 moles) of 2,3-dichlorophenol and 150 ml of 50% caustic soda. Mechanical stirring was commenced and 50 ml water added to dissolve the phenol more completely. Copper powder (0.4 g) was added and the solution warmed. Carbon tetrachloride 65 g (0.4 moles) was then added and the mixture refluxed for 48 hours.

After cooling the mixture was poured onto ice and acidified with concentrated hydrochloric acid to congo red. The solution was chilled in an ice bath and the precipitate filtered.

The red clay-like solid was dried and suspended in 200 ml of methylene chloride. After warming and stirring for 2 hours, the slurry was filtered. The precipitate was washed with a little methylene chloride and recrystallized from water after treatment with charcoal: yield 17.8 g, m.p. 200° (70% based on phenol consumed). From the methylene chloride washings, 13 g of starting phenol was recovered (60% conversion).

EXAMPLE 2

2,3-Dichloro-4-methoxybenzoic Acid

To 20.7 g (0.1 mole) off 2,3-dichloro-4-hydroxybenzoic acid was added 8 g of sodium hydroxide dissolved in 150 ml water. The solution was warmed to 60° and 12.6 g (0.1 mole) of dimethyl sulfate added. The mixture was then heated at 70° for 2 hours, cooled, acidified and filtered to yield 16.7 g. (75%) of the product, m.p. 224°-226°.

2,3-Dichloro-4-methoxybenzoic acid is then converted to tienilic acid by methods known to the art [for example, G, Thuillier, et al., *Eur. J. Med. Chem.*, 9, 625 (1974) ].

EXAMPLE 3

2,3-Dichloro-4-(2-thienoyl)-phenol

To a stirred slurry of thiophene 3 g (0.03 moles) and phosphorus pentoxide 3 g (0.02 moles) in 25 ml of benzene was added 4 g (0.02 moles) of 2,3-dichloro-4-hydroxybenzoic acid and the solution refluxed 4 hours. The benzene was evaporated and the residue was treated with water and filtered. The precipitate was recrystallized from methanol/water to yield 2 g of product, m.p. 138°-140°.

This compound (2,3-dichloro-4-(2-thienoyl)-phenol) is converted to tienilic acid by standard procedures. [U.S. Pat. No. 3,758,506 and *Eur. J. Med. Chem.*, 9, 625 (1974)].

What is claimed is:

1. The method of preparing 2,3-dichloro-4-hydroxybenzoic acid comprising reacting 2,3-dichlorophenol with an excess of carbon tetrachloride in the presence of an aqueous alkali metal hydroxide and copper powder at reflux until the reaction is completed.

2. 2,3-Dichloro-4-hydroxybenzoic acid.